(12) United States Patent
Gilligan et al.

(10) Patent No.: US 7,153,961 B2
(45) Date of Patent: Dec. 26, 2006

(54) SALT AND CRYSTALLINE FORM THEREOF OF A CORTICOTROPIN RELEASING FACTOR RECEPTOR ANTAGONIST

(75) Inventors: Paul J. Gilligan, Wilmington, DE (US); Shelly Renee Rabel Riley, Landenberg, PA (US); Paul A. Meenan, Mystic, CT (US)

(73) Assignee: Bristol-Myers Squibb Pharma Co., Princeton, NJ (US)

( * ) Notice: Subject to any disclaimer, the term of this patent is extended or adjusted under 35 U.S.C. 154(b) by 0 days.

(21) Appl. No.: 10/985,115

(22) Filed: Nov. 10, 2004

(65) Prior Publication Data

US 2005/0113375 A1 May 26, 2005

Related U.S. Application Data

(60) Provisional application No. 60/524,917, filed on Nov. 25, 2003.

(51) Int. Cl.
C07D 487/04 (2006.01)
A61K 31/53 (2006.01)
A61P 3/04 (2006.01)
A61P 25/22 (2006.01)
A61P 25/24 (2006.01)

(52) U.S. Cl. .................... 544/194; 514/246
(58) Field of Classification Search ............... 544/194; 514/245, 246
See application file for complete search history.

(56) References Cited

U.S. PATENT DOCUMENTS

| | | | | |
|---|---|---|---|---|
| 3,910,907 A | 10/1975 | O'Brien et al. | ............. | 260/248 |
| 4,824,834 A | 4/1989 | Fujii et al. | ................. | 514/246 |
| 4,892,576 A | 1/1990 | Kruger et al. | ................. | 71/93 |
| 5,137,887 A | 8/1992 | Hashimoto et al. | ......... | 514/246 |
| 5,484,760 A | 1/1996 | Bussler et al. | ............... | 504/103 |
| 6,060,478 A | 5/2000 | Gilligan et al. | ............. | 514/258 |
| 6,124,289 A | 9/2000 | He et al. | .................... | 514/245 |
| 6,136,809 A | 10/2000 | Gilligan et al. | ............. | 514/258 |
| 6,191,131 B1 | 2/2001 | He et al. | .................... | 514/246 |
| 6,313,124 B1 | 11/2001 | He et al. | .................... | 514/246 |
| 6,358,950 B1 | 3/2002 | He et al. | .................... | 514/246 |
| 2003/0125330 A1 | 7/2003 | Gilligan | ...................... | 514/246 |

FOREIGN PATENT DOCUMENTS

| | | |
|---|---|---|
| CN | 1 088 574 | 6/1994 |
| EP | 0 269 859 A2 | 6/1988 |
| EP | 0 594 149 A3 | 4/1994 |
| JP | 2001-302658 | 10/2001 |
| WO | WO 98/03510 | 1/1998 |
| WO | WO 98/08847 A1 | 3/1998 |
| WO | WO 01/23388 A3 | 4/2001 |
| WO | WO 02/72202 A1 | 9/2002 |

OTHER PUBLICATIONS

Mitchell, Neurosci. Biobehav. Rev. 22(5); 635-651, 1998.*
Albert, A.H., et al., "Synthesis of 2,4-dimethylpyrazolo[1,5-a]-1,2,5-triazine," *J. Het. Chem.*, 1973, p. 885.
Battaglia, G., et al., "characterization of corticotrophin-releasing factor receptor-mediated adenylate cyclase activity in the rat central nervous system," *Synapse*, 1987, 1, 572-581.
Beyer, H., et al., "Zur umsetzung von ketonitrilen mit hydrazinderivaten der kohlensäure," *Verlag Chemie GMBH Weinheim/Bergstr.,*, 1960, 9, 2209-2216.
Boissier, J.-R., et al., "A new method for rapid screening of minor transquillizers in mice," *Eur. J. of Pharmacol.*, 1968, 4, 145-151.
Bruni, F., et al., "Reactivity of 7-(2-dimethylaminovinyl)pyrazolo[1,5-a]pyrimidines: synthesis of pyrazolo[1,5-a][3,4-e]pyrimidine derivatives as potential benzodiazepine receptor ligands. 2.," *J. Heterocycl. Chem.*, 1995, 32, 291-298.
Collington, E.W., et al., "A facile and specific conversion of allylic alcohols to allylic chlorides," *J. Org. Chem.*, 1971, 36(20), 3044-3196.
Crossland, R.K., et al., "A facile synthesis of methanesulfonate esters," *J. Org. Chem.*, 1970, 35(9), 3195-3196.
Cusmano, S., et al., "Comportamento dei legami lidenici verso alcuni reattivi. Struttura delle sostanze ottenute per azione della semicarbazide sui benzalderivati di corpi β-chetonitriliei—Nota V.," *Gazz. Chim. Ital.*, 1952, 82, 373-384 (Italian).
Dunn, A.J., et al., "Physiological and behavioral responses to corticotrophin-releasing factor administration: is CRF a mediator of anxiety or stress responses," *Brain Res. Rev.*, 1990, 15, 71-100.
Funk, D., et al., "Role of catecholamines in the frontal cortex in the modulation of basal and stress-induced autonomic output in rats," *Brain Res.*, 1996, 741, 220-229.
Griebel, G., et al., "Genetic differences in the mouse defense test battery," *Aggress. Behav.*, 1997, 23, 19-31.
Grigoriadis D.E., et al., "Corticotropin-releasing factor (CRF) receptors in intermediate lobe of the pituitary: biochemical chjaracterization and autoradiographic localization," *Peptides*, 1989, 10, 179-188.
He, L., et al., "4-(1,3-dimethoxyprop-2-ylamino)-2,7-dimethyl-8-(2,4-dichlorophenyl)-pyrazolo[1,5-*a*]-1,3,5-triazine: a potent, orally bioavailable $CRF_1$ receptor," *J. Med. Chem.*, 2000, 43, 449-456.
Kobe, J., et al., "The chemistry of 4-hydrazino-7-phenylpyrazolo[1,5-a]-1,3,5-triazines," *J. Het. Chem.*, 1974, 991-996.
Kobe, J., et al., "The synthesis and chemical reactions of certain pyrazolo[1,5-a]-1,3,5-traizines(1)," *J. Het. Chem.*, 1974, 199-204.
Meyers, A.I., et al., "An efficient total synthesis of propylure, the highly active sex attractant for the pink bollworm moth," *Tetrahedron*, 1971, 27, 5979-5985.

(Continued)

*Primary Examiner*—Venkataraman Balasubramanian
(74) *Attorney, Agent, or Firm*—Shah R. Makujina; Woodcock Washburn, LLP

(57) ABSTRACT

The present invention provides 4-(bis(2-methoxyethyl) amino)-2,7-dimethyl-8-(2-methyl-4-methoxyphenyl)-[1,5-a]-pyrazolo-1,3,5-triazine benzenesulfonate salt and a crystalline polymorph thereof. Further provided are pharmaceutical compositions containing the salt and methods of treating CRF-related disorders using said salt.

11 Claims, 2 Drawing Sheets

OTHER PUBLICATIONS

Misslin, R., et al., "Behavioural validation of a light/dark choice procedure for testing anti-anxiety agents," *Behav. Process*, 1989, 18, 119-132.

Munson, P.J., et al., "LIGAND: A versatile computerized approach for characterization of ligand-binding systems," *Anal. Biochem.*, 1980, 107, 220-239.

Nagel, D.L., et al., "Synthesis of alkyl-substituted benzo[c]phenanthrenes and chrysenes by photocyclization," *J. Org. Chem.*, 1977, 42(22), 3626-3628.

Nishida, A., et al., "Rotational isomerism in fluorine derivatives XIV conformational equillbria of β-substituted 9-(2-cyanomethylphenyl) fluorine derivatives," *Technol. Rep. Yamaguchi Univ.*, 1988, 4(2), 145-150.

Novinson, T., et al., "synthesis of unsymmetrical 2,4-dialkylpyrazolo[1,5-a]-1,3,5-triazines," *J. Het. Chem.*, 1974, 691-695.

Pellow, S., et al., "Validation of open: closed arm entries in an elevated plus-maze as a measure of anxiety in the rat," *J. of Neurosci. Methods*, 1985, 14, 149-167.

Page, G.A., et al., "The synthesis of benzcyclohepten-6-one," *J. Am. Chem. Soc.*, 1953, 75, 2053-2055.

Pietraszuk, C., et al., "Cross-metathesis of vinylsilanes with olefins in the presence of Grubbs' catalyst," *Tetrahedron Lett.*, 2001, 42, 1175-1178.

Porsolt, R.D., et al., "Depression: a new animal model sensitive to antidepressant treatment," *Nature*, 1977, 266, 730-732.

Principles of Process Research and Chemical Development in the Pharmaceutical Industry, *Wiley*, 1998, p. 38-40.

Rapoport, H., et al., "The synthesis of 2,3,4-trimethoxybenzcyclohepten-6-one," *J. Am. Chem. Soc.*, 1951, 73, 2239-2241.

Senga, K., et al., "Synthesis and enzymic activity of various substituted pyrazolo[1,5-a]-1,3,5-triazines as adenosine cyclic 3',5'-phosphate phosphodiesterase inhibitors," *J. Med. Chem.*, 1982, 25, 243-249.

Stogryn, E.L., "A new synthesis of 3,4-(difluoromethylenedioxy)benzaldehydr," *J. Org. Chem.*, 1972, 37(4), p. 673.

Vogel, J.R., et al., "A simple and reliable conflict procedure for testing anti-anxiety agents," *Psychopharmcologia (Berl.)*, 1971, 21, 1-7.

Willner, P., et al., "An animal model of anhedonia," *Clin. Neuropharmacol.*, 1992, 15(suppl. 1), 550A-551A.

Wynn, P.C., et al., "Regulation of corticotrophin-releasing factor (CRF) receptors in the rat pituitary gland: effects of adrenalectomy on CRF receptors and corticotroph responses,"*Endocrinology*, 1985, 116(4), 1653-1659.

Logemann, W., et al., "Studien in der heterocyclischen reihe, II. Mitteil.*): Die synthese von 1.3.5-triazine und 5-oxy-isoxazol-derivaten," *Chem. Ber.*, 1954, 87, 1175-1179 (German).

Bellec, C., et al., "Structure de derives de β- cétonitriles. II. Tautomérie hydrazone-énehydrazine; etude des configurations," *Beilstein Institut. Zur Foerderung Der*, Accession No. 3384927, 1988, II-441-II-448 (Summary in English).

Souchay, et al., "CHDCAQ," *S.R.Hebd. Seances Acad. Sci. Ser. C*, 1973, p. 1457 (Accession No. 2981462, 1 page).

Yamashita, M., "BCSJA8," *Bull. Chem. Soc. Jpn.*, 1941, 16, 413-415 (Accession No. 3384927, 1 page).

* cited by examiner

US 7,153,961 B2

SALT AND CRYSTALLINE FORM THEREOF OF A CORTICOTROPIN RELEASING FACTOR RECEPTOR ANTAGONIST

CROSS-REFERENCE TO RELATED APPLICATIONS

This application claims priority to U.S. Provisional Application Ser. No. 60/524,917, filed Nov. 25, 2003, the disclosure of which is incorporated herein by reference in its entirety.

FIELD OF THE INVENTION

The present invention generally relates to the benzenesulfonate salt of 4-(bis(2-methoxyethyl)amino)-2,7-dimethyl-8-(2-methyl-4-methoxyphenyl)-[1,5-a]-pyrazolo-1,3,5-triazine. The present invention also relates to pharmaceutical compositions comprising the same and methods of using the same.

BACKGROUND OF THE INVENTION

Corticotropin releasing factor (CRF) is a 41 amino acid peptide that coordinates the overall response of the body to stress. As an agonist of CRF receptors (e.g., $CRF_1$ and $CRF_2$), CRF is well known as the primary physiological secretagogue controlling hypothalamic-pituitary-adrenal (HPA) axis activity which mediates the endocrine stress response. CRF also plays a central role in the autonomic and behavioral responses to stress. Variation in physiological levels of CRF has been correlated with various disorders including depression and anxiety.

Antagonists of CRF receptors have been shown to effectively ameliorate behavioral stress responses in animal models. It is well established that systemic administration of $CRF_1$ receptor antagonists leads to anxiolytic and antidepressant effects in rodents. Animal model evidence also shows that $CRF_1$ antagonists can help alleviate the symptoms of drug withdrawal, stress-induced seizures, and certain inflammations. A role for CRF has also been postulated in the etiology and pathophysiology of Alzheimer's disease, Parkinson's disease, Huntington's disease, progressive supranuclear palsy, and amyotrophic lateral sclerosis as they relate to the dysfunction of CRF neurons in the central nervous system. Eating disorders, such as anorexia nervosa, have also been linked to elevated levels of CRF.

Though widely dispersed throughout the central nervous system, CRF receptors are also found in peripheral systems including glandular, vascular, gastrointestinal, and immune system tissues. Accordingly, CRF antagonists are believed to have potential in treating numerous other disorders outside the central nervous system. Some CRF-related disorders of peripheral systems include, for example, hypertension, tachycardia, congestive heart failure, stroke, irritable bowel syndrome, post-operative ileus, and colonic hypersensitivity. Studies have indicated that $CRF_1$ antagonists may also be useful as hair growth stimulators.

The compound 4-(bis(2-methoxyethyl)amino)-2,7-dimethyl-8-(2-methyl-4-methoxyphenyl)-[1,5-a]-pyrazolo-1,3,5-triazine has been identified as an effective CRF receptor antagonist that can be useful in treating, for example, the above-named disorders. This compound is reported in U.S. Pat. No. 6,124,289 which is incorporated herein by reference in its entirety.

While numerous CRF receptor antagonists have been discovered, like the above compound, few typically possess the characteristics that are satisfactory for the preparation of stable pharmaceutical compositions. Melting point, hygroscopicity, stability, solubility, crystallinity, bioavilability, and handling characteristics are among the numerous properties that need to be considered in preparing medicaments that can be effectively administered. Accordingly, there is an ongoing need to prepare compounds with physical and chemical properties that are both physiologically acceptable and suitable for preparing reproducible pharmaceutical formulations. The salts of the present invention helps fulfill this and other needs.

SUMMARY OF THE INVENTION

The present invention provides a compound which is a benzenesulfonate salt of 4-(bis(2-methoxyethyl)amino)-2,7-dimethyl-8-(2-methyl-4-methoxyphenyl)-[1,5-a]-pyrazolo-1,3,5-triazine, including hydrates and solvates thereof. According to some embodiments, the salt is a hydrate according to Formula I below having n water molecules where n is from 0 to 1. Additionally, the salt can have a differential scanning calorimetry thermogram substantially as shown in FIG. 2 and/or a differential scanning calorimetry thermogram with a maximum at about 94° C.

According to some embodiments, the salts of the invention are crystalline and can have an X-ray powder diffraction spectrum substantially as shown in FIG. 1. In some embodiments, the salts of the invention have an X-ray powder diffraction spectrum having peaks according to the 2-theta values listed below in Table 1a. In other embodiments, the X-ray powder diffraction spectrum comprises peaks at 2-theta values of 6.7±0.2°, 10.4±0.2°, 11.7±0.2°, and 22.2±0.2° or the X-ray powder diffraction spectrum comprises four or more peaks at 2-theta values selected from the group consisting of 6.7±0.2°, 8.0±0.2°, 10.4±0.2°, 11.7±0.2°, 22.2±0.2°, 12.3±0.2°, 12.5±0.2°, 13.2±0.2°, 15.7±0.2°, 16.9±0.2°, 18.8±0.2°, 21.1±0.2°, 21.3±0.2°, 23.0±0.2°, 24.0±0.2°, 24.2±0.2°, and 26.8±0.2°.

According to some embodiments, the salts of the present invention can crystallize in space group $P2_1/n$ and having the following unit cell parameters: a is about 14.4 Å; b is about 9.1 Å; c is about 22 Å; and β is about 102°.

In further embodiments, the salts of the invention can have a $^{13}C$ solid state nuclear magnetic resonance spectrum comprising four or more resonance peaks selected from the group consisting of 11.7±0.2, 19.2±0.2, 21.8±0.2, 56.0±0.2, 54.0±0.2, 59.2±0.2, 60.3±0.2, 71.8±0.2, 73.5±0.2, 104.9±0.2, 112.7±0.2, 114.5±0.2, 119.7±0.2, 126.4±0.2, 128.8±0.2, 129.7±0.2, 131.6±0.2, 139.1±0.2, 141.3±0.2, 146.0±0.2, 147.8±0.2, 154.6±0.2, 160.7±0.2, and 161.8±0.2 ppm.

The present invention additionally provides compositions comprising the salts of the present invention and a pharmaceutically acceptable carrier.

Further embodiments include methods of treating a disorder in a mammal characterized by abnormal levels of CRF, comprising administering to the mammal a therapeutically effective amount of a salt of the present invention. Accordingly, the present invention further provides methods of treating anxiety or depression or irritable bowel syndrome in a mammal comprising administering to the mammal a therapeutically effective amount of a salt of the present invention.

DETAILED DESCRIPTION OF PREFERRED EMBODIMENTS

The present invention provides, inter alia, a benzenesulfonate salt of 4-(bis(2-methoxyethyl)amino)-2,7-dimethyl-8-(2-methyl-4-methoxyphenyl)-[1,5-a]-pyrazolo-1,3,5-triazine. The salt can include any hydrate (e.g., hemi-, mono-, di-, etc.) or solvate form thereof.

According to some embodiments of the present invention, the salt of Formula I can be amorphous, and in other embodiments, the salt of Formula I can be crystalline. Crystalline forms (polymorphs) can be obtained by any method known in the art, such as, for example, by dissolving the salt in an appropriate solvent and then cooling the solution. Alternatively, precipitation can be induced by combining the solution with an additional solvent in which the salt is less soluble. The salt of Formula I can be crystallized from isopropyl acetate or ethyl acetate, for example. Precipitation/crystallization from these solvents can be optionally induced by precipitation with heptane or other non-polar solvents to yield a colorless/off-white crystalline product.

According to some embodiments, the above salt can be obtained as a crystalline polymorph (Form H-1) crystallized from, for example, isopropyl acetate or ethyl acetate solvent. Based on single crystal X-ray diffraction studies, the H-1 polymorph can form crystals having monoclinic space group $P2_1/n$ with the following unit cell parameters: a is about 14.4 Å; b is about 9.1 Å; c is about 22 Å; and $\beta$ is about 102°. The three-dimensional structure reveals a hydrate with only partial occupancy of one identified water molecule site. At about 22° C., water occupancy can be about 0.4 whereas at about −100° C., water occupancy can be about 0.75.

In accordance with certain preferred embodiments, salts of Formula I may be in substantially pure form. As used herein "substantially pure" means a compound having a purity greater than 90 percent, including 90, 91, 92, 93, 94, 95, 96, 97, 98, 99, and 100 percent.

In some embodiments, the salts of the present invention can be compounds of Formula I:

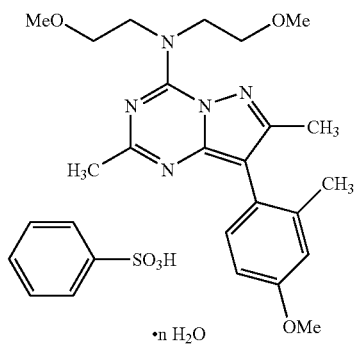

where n is from about 0 to about 1. For example, n can be from about 0.3 to about 0.9, about 0.4 to about 0.8, or about 0.5 to about 0.7.

Figure 1:
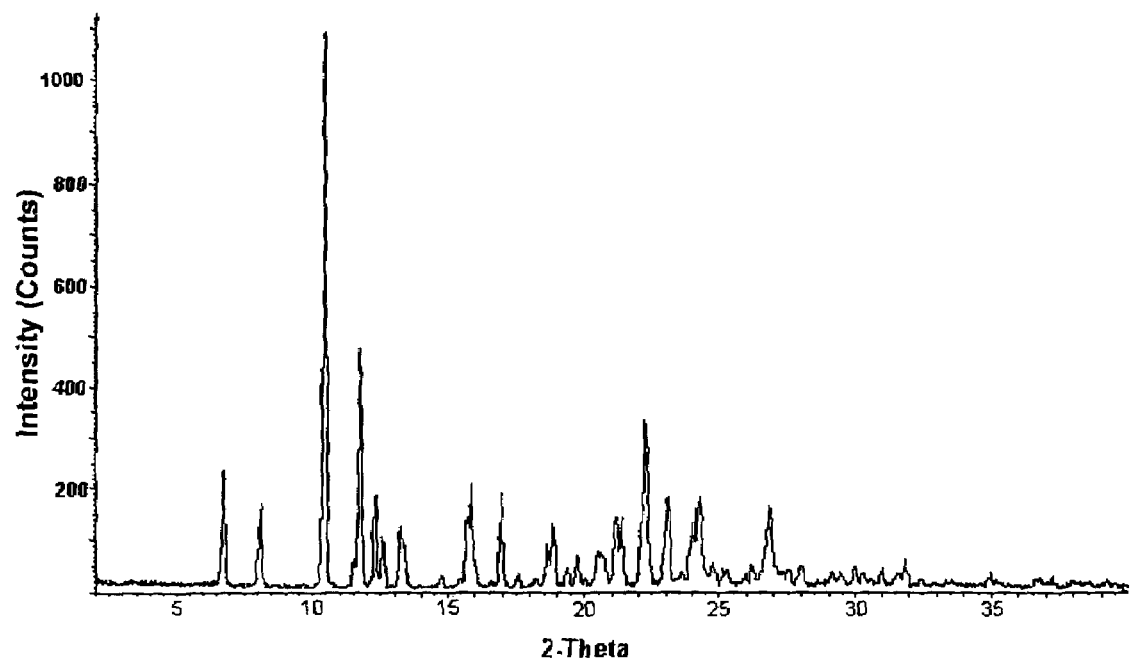
FIG. 1 depicts an X-ray powder diffraction pattern characteristic of the H-1 crystalline polymorph according to embodiments of the present invention.

The H-1 polymorph can be characterized by the X-ray powder diffraction (XRPD) spectrum of FIG. 1 obtained using CuKα radiation ($\lambda$=0.15046 nm). A summary of XRPD data, listing 2-theta values and relative intensities for observed reflections, is provided below in Table 1. According to some embodiments of the present invention, the salts of Formula I can have an XRPD spectrum having at least 5, at least 10, at least 15, at least 20, at least 25, or all of the peaks listed in Table 1. In some embodiments, the salts of Formula I can have an XRPD spectrum comprising at least the peaks of Table 1 with high intensities (e.g., 6.7±0.2°, 10.4±0.2°, 11.7±0.2°, and 22.2±0.2°), or comprising the peaks of Table 1 with high or medium intensities (6.7±0.2°, 8.0±0.2°, 10.4±0.2°, 11.7±0.2°, 22.2±0.2°, 12.3±0.2°, 12.5±0.2°, 13.2±0.2°, 15.7±0.2°, 16.9±0.2°, 18.8±0.2°, 21.1±0.2°, 21.3±0.2°, 23.0±0.2°, 24.0±0.2°, 24.2±0.2°, and 26.8±0.2°). In some embodiments, the salt of Formula I has an XRPD spectrum substantially as shown in FIG. 1.

TABLE 1

| 2-theta (°) | Intensity[a] |
|---|---|
| 6.7 ± 0.2 | high |
| 8.0 ± 0.2 | medium |
| 10.4 ± 0.2 | high |
| 11.7 ± 0.2 | high |
| 12.3 ± 0.2 | medium |
| 12.5 ± 0.2 | medium |
| 13.2 ± 0.2 | medium |
| 14.6 ± 0.2 | low |
| 15.7 ± 0.2 | medium |
| 16.9 ± 0.2 | medium |
| 17.5 ± 0.2 | low |
| 18.1 ± 0.2 | low |
| 18.6 ± 0.2 | low |
| 18.8 ± 0.2 | medium |
| 19.3 ± 0.2 | low |
| 19.7 ± 0.2 | low |
| 20.5 ± 0.2 | low |
| 21.1 ± 0.2 | medium |
| 21.3 ± 0.2 | medium |
| 22.2 ± 0.2 | high |
| 23.0 ± 0.2 | medium |
| 23.5 ± 0.2 | low |
| 24.0 ± 0.2 | medium |
| 24.2 ± 0.2 | medium |
| 24.7 ± 0.2 | low |
| 25.2 ± 0.2 | low |
| 25.9 ± 0.2 | low |
| 26.2 ± 0.2 | low |
| 26.8 ± 0.2 | medium |
| 27.5 ± 0.2 | low |
| 27.9 ± 0.2 | low |

[a]high is ≧250 counts (21.7%); medium is 100–249 counts (21.7 to 8.7%); low is <100 counts (8.7%).

Polymorph H-1 can be further characterized by solid state $^{13}$C nuclear magnetic resonance ($^{13}$C SSNMR). Resonance peaks in the spectrum comprise four or more of the following: 11.7±0.2, 19.2±0.2, 21.8±0.2, 56.0±0.2, 54.0±0.2, 59.2±0.2, 60.3±0.2, 71.8±0.2, 73.5±0.2, 104.9±0.2, 112.7±0.2, 114.5±0.2, 119.7±0.2, 126.4±0.2, 128.8±0.2, 129.7±0.2, 131.6±0.2, 139.1±0.2, 141.3±0.2, 146.0±0.2, 147.8±0.2, 154.6±0.2, 160.7±0.2, and 161.8±0.2 ppm. According to some embodiments, the $^{13}$C solid state NMR spectrum of the salt of Formula I comprises at least 5, at least 10, at least 15, or at least 20 of the above recited peaks.

Figure 2:
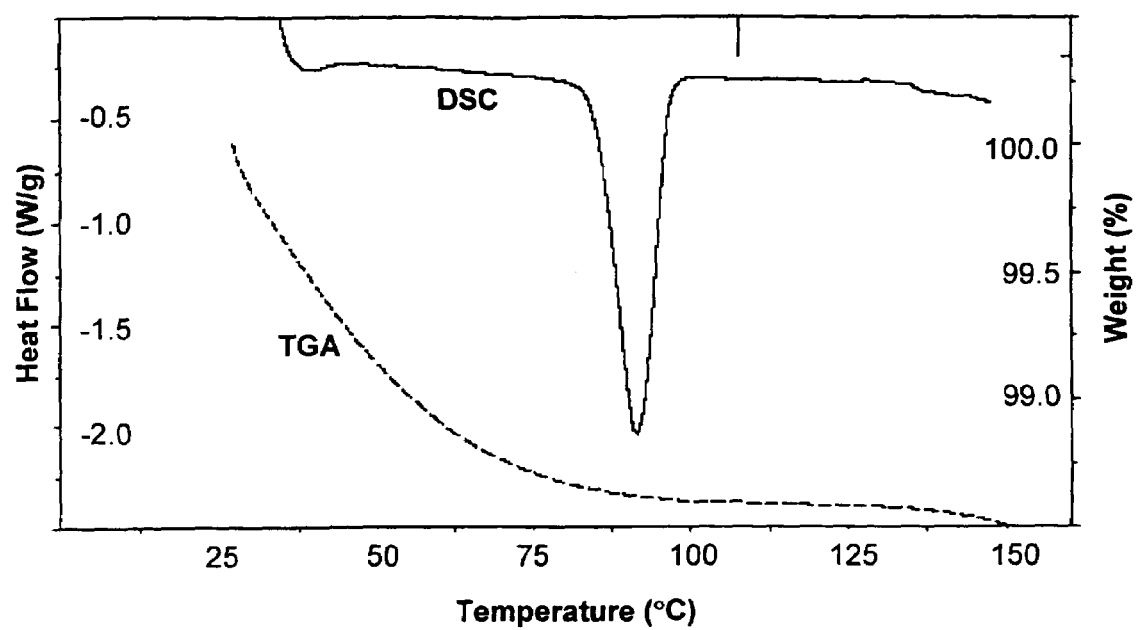
FIG. 2 depicts a combined differential scanning calorimetry thermogram and thermogravimetric analysis for the H-1 polymorph according to embodiments of the present invention.

Polymorph H-1 can be further characterized by the differential scanning calorimetry (DSC) thermogram depicted in FIG. 2 which shows a maximum at about 94° C. Accordingly, embodiments of the present invention include a salt of Formula I having a thermogram substantially as shown in FIG. 2 and/or a thermogram having a maximum at about 94° C. Also shown in FIG. 2 are the results of thermogravimetric analysis (TGA) of polymorph H-1. Weight loss can vary, for example, from about 0.7 to about 1.5%, according to batch.

The salts of the present invention, including crystalline polymorph H-1, are suitable for preparing stable and effective pharmaceutical compositions. Example properties which make the present salts suitable for the preparation of pharmaceutical compositions include a suitably high melting point (occurring between about 90 and 100° C.), low hygroscopicity (shown to be about less than 2% uptake at 90% relative humidity), and suitable solubility (soluble in e.g., polar solvents, water, glycols, and aqueous mixtures).

Accordingly, the present invention further provides pharmaceutical compositions comprising a benzenesulfonate salt of 4-(bis(2-methoxyethyl)amino)-2,7-dimethyl-8 -(2-methyl-4-methoxyphenyl)-[1,5-a]-pyrazolo-1,3,5-triazine, such as, for example, a salt of Formula I, and a pharmaceutically acceptable carrier. The compositions can comprise the salt in amorphous form or in crystalline form, such as polymorph H-1.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

The present invention also includes methods of treating a disorder characterized by abnormal levels of corticotropin releasing factor in a mammal by administering to the mammal a therapeutically effective amount of salt of the present invention, such as a salt of Formula I, or a composition containing a salt of the present invention. According to some embodiments, the disorder can be characterized by elevated levels of corticotropin releasing factor. In some embodiments, the disorder affects the central nervous system. Example disorders of the central nervous system that can be treated according to the methods described herein include anxiety or depression. In other embodiments, the disorder affects peripheral systems. Accordingly, an example of a treatable disorder of the peripheral systems according to the methods described herein is irritable bowel syndrome.

Some disorders characterized by abnormal levels of corticotropin releasing factor include the following disorders: mood disorders such as depression, including major depression, single episode depression, recurrent depression, child abuse induced depression, seasonal affective disorder, postpartum depression, dysthemia, bipolar disorders, and cyclothymia; anxiety disorders including panic, phobias, obsessive-compulsive disorder; post-traumatic stress disorder; and sleep disorders induced by stress; inflammation; pain; chronic fatigue syndrome; stress-induced headache; cancer; human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ileus, and colonic hypersensitivity associated by psychopathological disturbances or stress; eating disorders such as anorexia and bulimia nervosa; supranuclear palsy; amyotrophic lateral sclerosis; immune suppression; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular disorders including hypertension, tachycardia and congestive heart failure; stroke; immune dysfunctions including stress-induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism; hypoglycemia; hair loss; abnormal circadian rhythm; and disorders related to abnormal circadian rhythm such as time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia, and abnormal circadian rhythm associated with chronic administration and withdrawal of antidepressant agents. Thus, the compounds provided herein, because of their antagonism of CRF receptors, are expected to be useful in treating these and other disorders.

The term "therapeutically effective amount" refers to an amount of salt effective to reduce or eliminate at least one symptom of a disorder that the salt was used to treat.

A salt of the present invention can be administered to treat the above disorders by any suitable means that allows the compound to contact the salts' site of action, such as a CRF receptor, in the body of a mammal. The salt can be administered by any conventional means available for use in conjunction with pharmaceuticals either as an individual therapeutic agent or in combination with other therapeutic agents. The salts of the present invention can be administered alone, or in combination with a pharmaceutical carrier selected on the basis of the chosen route of administration and standard pharmaceutical practice.

The dosage of salt for administration varies depending on several factors such as the pharmacodynamic character of the particular compound, and its mode and route of administration; the recipient's age, weight, and health; nature and extent of symptoms; kind of concurrent treatment; frequency of treatment; and desired effect. For use in the treatment of the above diseases or conditions, the salts of this invention can be orally administered daily at a dosage of the active ingredient (e.g., a salt of Formula I) of about 0.002 to about 200 mg/kg of body weight. For example, a dose of about 0.01 to about 10 mg/kg can be divided into smaller doses and administered one to four times a day. Alternatively, sustained release formulations can be effective in obtaining the desired pharmacological effect.

Dosage forms (compositions) suitable for administration can contain from about 1 mg to about 100 mg of active ingredient per dosage unit. In these pharmaceutical compositions, the active ingredient (e.g., a salt of Formula I) can be present in an amount of about 0.5 to 95% by weight based on the total weight of the composition.

The active ingredient (e.g., a salt of Formula I) can be administered orally in solid dosage forms such as capsules, tablets and powders, or in liquid forms such as elixirs, syrups, and/or suspensions. The salts of this invention can also be administered parenterally in sterile liquid dose formulations.

Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can also contain coloring or flavoring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water soluble salt of the active ingredient and suitable stabilizing agents. Antioxidizing agents, such as sodium bisulfite, sodium sulfite, or ascorbic acid, either alone or in combination, can act as suitable stabilizing agents. Also suitable as stabilizing agents are citric acid and its salts, and EDTA. In addition, parenteral solutions can contain preservatives such as, for example, benzalkonium chloride, methyl- or propyl-paraben, and chlorobutanol.

The techniques used to characterize the salts and polymorph described herein are well known to the skilled artisan. As those skilled in the art will appreciate, numerous changes and modifications can be made to the embodiments of the invention without departing from the spirit of the invention. It is intended that all such variations fall within the scope of the invention.

It is intended that each of the patents, applications, and printed publications mentioned in this patent document be hereby incorporated by reference in its entirety.

EXAMPLES

Example 1

Preparation of Intermediate
2-(4-methoxy-2-methylphenyl)-3-oxobutyronitrile
potassium salt

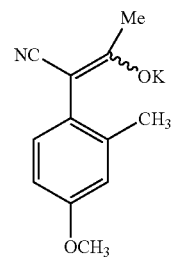

Under anhydrous conditions, (4-methoxy-2-methylphenyl)acetonitrile (25.0 kg, 155 moles, available commercially) and 68.3 kg of ethyl acetate were mixed to obtain a solution. The resulting solution was heated to 35° C. and potassium t-butoxide in THF (100 kg, 20 wt %, 178 moles) was added over a 30 to 60 minute period controlling the temperature at 35° C. Following the addition, the reaction mass was heated to 45° C. and held for 60 minutes. At the end of the hold period, a sample was analyzed by HPLC. The reaction mixture was then cooled to 25° C. and combined with 3 other batches for a total of 843 kg of solution.

Example 2

Preparation of Intermediate
2-(4-methoxy-2-methylphenyl)-3-oxobutyronitrile
semicarbazone

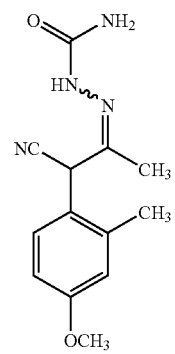

Four batches of the solution prepared according to Example 1 and water (150 kg) were combined. Solvent (557 kg) was distilled from the mixture at 145 mm Hg and 35° C. Next, water (1200 kg), acetic acid (47.0 kg), semicarbazide hydrochloride (89.0 kg, 798 moles) and IPA (475 kg) were added. The resulting mixture was heated to 25–35° C. and held for 21 hours. The reaction was monitored by HPLC. The 2-(4-methoxy-2-methylphenyl)-3-oxobutyronitrile semicarbazone formed was isolated by filtration and the cake washed with water (2×250 kg). A total of 143 kg was isolated. The purity was 99.3 wt %. The yield was 93.1% of theoretical.

Example 3

Preparation of Intermediate 5-amino-4-(4-methoxy-2-methylphenyl)-3-methylpyrazole-1-carboxylic acid amide

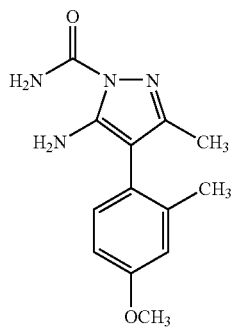

2-(4-methoxy-2-methylphenyl)-3-oxobutyronitrile semicarbazone (160 g, 615 mmol) of Example 2 and N-methylpyrrolidinone (NMP, 480 mL) were charged and the resulting slurry was cooled to <5° C. 1,8-Diazabicyclo[5.4.0]undec-7-ene (DBU, 18.0 mL, 120 mmol) was added. The reaction mass was held at <5° C. for 1.0 to 1.5 hours. Conversion to 5-amino-4-(4-methoxy-2-methylphenyl)-3-methylpyrazole-1-carboxylic acid amide was monitored by HPLC (typically greater than 95%).

Example 4

Preparation of Intermediate 8-(4-methoxy-2-methylphenyl)-2,7-dimethylpyrazolo [1,5-a][1,3,5]triazin-4-ol.

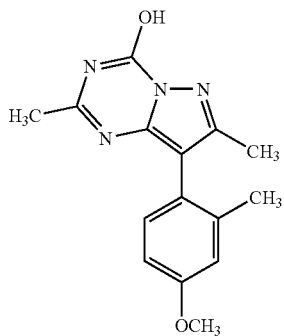

p-Toluenesulfonic acid (29.2 g, 154 mmol) in acetonitrile (100 mL) was added to the reaction mixture described in Example 3 containing 5-amino-4-(4-methoxy-2-methylphenyl)-3-methylpyrazole-1-carboxylic acid amide. The resulting mixture was heated to 85–90° C. and trimethyl orthoacetate (160 mL, 1.26 mol) was added over 5 minutes during the heating. The reaction was held for about 45 minutes in the desired range with a total of 1.5 hours of heating time from the initiation of the heating cycle. Reaction progress was monitored by HPLC. Water (1.50 L) was added over 5 minutes with a temperature drop to about 60° C. The resulting mixture was cooled to about 20° C. over 1 hour and the product isolated by filtration. The yield was 136 g (78.0% with a purity of 99.5 A %).

Example 5

Preparation of 4-(bis(2-methoxyethyl)amino)-2,7-dimethyl-8-(2-methyl-4-methoxyphenyl)-[1,5-a]-pyrazolo-1,3,5-triazine benzenesulfonate (I).

8-(4-Methoxy-2-methylphenyl)-2,7-dimethylpyrazolo[1,5-a][1,3,5]triazin-4-ol of Example 4 (50.0 g, 176 mmol), benzyltriethylammonium chloride (30.0 gm, 132 mmol), isopropyl acetate (200 mL) and acetonitrile (50 mL) were charged and the resulting slurry treated with N,N-diisopropylethyl amine (45.9 mL, 264 mmol) and phosphorous oxychloride (24.6 mL, 264 mmol). The resulting mixture was heated to 65° C. and held for about 1.5 hr at which time the reaction was complete. The mixture was cooled to about 10° C. and treated with bis-(2-methoxyethyl)amine (64.9 mL, 440 mmol) for about 30 min. The resulting reaction mixture was quenched into aqueous sodium hydroxide at about 40° C., and the organic portion washed with water, aqueous citric acid and water. The solution yield of the free base was about 85% of theoretical over the sequence.

The salt was prepared by dissolving benzenesulfonic acid (30.0 g, 190 mmol) in isopropyl acetate (50 mL) and adding this resulting solution to the mixture obtained above. The salt precipitated and was collected by filtration.

Example 6

Preparation of Polymorph H-1

Polymorph H-1 was prepared by recrystallization of the crude material from Example 5 with three volumes of isopropyl acetate at 60° C. and cooled slowly to 10° C. where the product was collected by filtration.

Example 7

X-Ray Powder Diffraction

X-ray powder diffraction data was obtained with a Bruker AXS D8 Advance automated powder diffractometer. The diffractometer was equipped with a variable slit (q-compensating slit), a scintillation counter and a graphite monochromator. The radiation was CuKa (40 kV, 40 mA). Data were collected at room temperature from 2 to 40 degrees 2 theta; the step size was 0.02 degrees; the step time was 0.4 sec. per step. Samples were prepared on glass specimen holders as a thin layer of powdered material without solvent.

Example 8

Differential Scanning Calorimetry

Differential scanning calorimetry was carried out using a Mettler 850, TA 2920 or equivalent. Samples were placed in sealed aluminum pans for analysis with an empty aluminum pan serving as the reference. A heating rate of 10° C. per minute was employed over a temperature range of 25° C. to 150° C.

Example 9

Thermogravimetric Analysis (TGA)

The thermogravimetric analysis was conducted on a Mettler 850, TA instruments 2950 or equivalent. Samples were placed into a ceramic or aluminum sample pan. A heating rate of 10° C. per minute were employed over a temperature range of 25° C. to 150° C.

What is claimed is:

1. A compound which is a hydrate of a benzenesulfonate salt of 4-(bis(2-methoxyethyl)amino)-2,7-dimethyl-8-(2-methyl-4-methoxyphenyl)-[1,5-a]-pyrazolo-1,3,5-triazine.

2. The compound of claim 1 having Formula I:

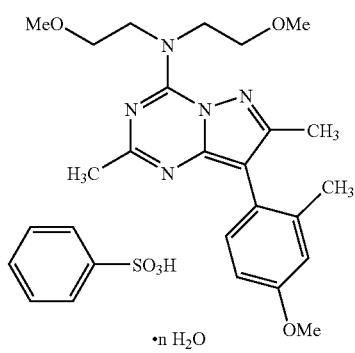

I

•n $H_2O$ wherein n is from about 0.3 to about 0.9.

3. The compound of claim 1 having a differential scanning calorimetry thermogram substantially as shown in FIG. 2.

4. The compound of claim 1 having a differential scanning calorimetry thermogram with a maximum at about 94° C.

5. The compound of claim 1 wherein said compound is crystalline.

6. The compound of claim 5 having an X-ray powder diffraction spectrum substantially as shown in FIG. 1.

7. The compound of claim 5 having an X-ray powder diffraction spectrum having peaks comprising four or more 2-theta values listed below in Table 1a:

TABLE 1a

| 2-theta (°) |
| --- |
| 6.7 ± 0.2 |
| 8.0 ± 0.2 |
| 10.4 ± 0.2 |
| 11.7 ± 0.2 |
| 12.3 ± 0.2 |

TABLE 1a-continued

| 2-theta (°) |
| --- |
| 12.5 ± 0.2 |
| 13.2 ± 0.2 |
| 14.6 ± 0.2 |
| 15.7 ± 0.2 |
| 16.9 ± 0.2 |
| 17.5 ± 0.2 |
| 18.1 ± 0.2 |
| 18.6 ± 0.2 |
| 18.8 ± 0.2 |
| 19.3 ± 0.2 |
| 19.7 ± 0.2 |
| 20.5 ± 0.2 |
| 21.1 ± 0.2 |
| 21.3 ± 0.2 |
| 22.2 ± 0.2 |
| 23.0 ± 0.2 |
| 23.5 ± 0.2 |
| 24.0 ± 0.2 |
| 24.2 ± 0.2 |
| 24.7 ± 0.2 |
| 25.2 ± 0.2 |
| 25.9 ± 0.2 |
| 26.2 ± 0.2 |
| 26.8 ± 0.2 |
| 27.5 ± 0.2 |
| 27.9 ± 0.2. |

8. The compound of claim 5 having an X-ray powder diffraction spectrum comprising peaks at 2-theta values of 6.7±0.2°, 10.4±0.2°, 11.7±0.2° and 22.2±0.2°.

9. The compound of claim 5 having an X-ray powder diffraction spectrum comprising four or more peaks at 2-theta values selected from the group consisting of 6.7±0.2°, 8.0±0.2°, 10.4±0.2°, 11.7±0.2°, 22.2±0.2°, 12.3±0.2°, 12.5±0.2°, 13.2±0.2°, 15.7±0.2°, 16.9±0.2°, 18.8±0.2°, 21.1±0.2°, 21.3±0.2°, 23.0±0.2°, 24.0±0.2°, 24.2±0.2°, and 26.8±0.2°.

10. The compound of claim 5 crystallizing in space group $P2_1/n$ and having the following unit cell parameters: a is about 14.4 Å; b is about 9.1 Å; c is about 22 Å; and β is about 102°.

11. The compound of claim 5 having a $^{13}C$ solid state nuclear magnetic resonance spectrum comprising four or more resonance peaks selected from the group consisting of 11.7±0.2, 19.2±0.2, 21.8±0.2, 56.0±0.2, 54.0±0.2, 59.2±0.2, 60.3±0.2, 71.8±0.2, 73.5±0.2, 104.9±0.2, 112.7±0.2, 114.5±0.2, 119.7±0.2, 126.4±0.2, 128.8±0.2, 129.7±0.2, 131.6±0.2, 139.1±0.2, 141.3±0.2, 146.0±0.2, 147.8±0.2, 154.6±0.2, 160.7±0.2, and 161.8±0.2 ppm.

* * * * *